US 007750626B2

(12) United States Patent
Lefebvre et al.

(10) Patent No.: US 7,750,626 B2
(45) Date of Patent: Jul. 6, 2010

(54) METHOD AND APPARATUS FOR EDDY CURRENT DETECTION OF MATERIAL DISCONTINUITIES

(75) Inventors: J. H. Vivier Lefebvre, Gatineau (CA); Catalin V. Mandache, Ottawa (CA)

(73) Assignees: Her Majesty the Queen in right of Canada, as represented by the Minister of National Defence of Her Majesty's Canadian Government, Ottawa, Ontario (CA); National Research Council of Canada, Ottawa, Ontario (CA)

( * ) Notice: Subject to any disclaimer, the term of this patent is extended or adjusted under 35 U.S.C. 154(b) by 58 days.

(21) Appl. No.: 11/372,126

(22) Filed: Mar. 10, 2006

(65) Prior Publication Data

US 2006/0202689 A1    Sep. 14, 2006

Related U.S. Application Data

(60) Provisional application No. 60/661,033, filed on Mar. 14, 2005.

(51) Int. Cl.
*G01N 27/82* (2006.01)
*G01R 33/12* (2006.01)

(52) U.S. Cl. .................... 324/240; 324/233
(58) Field of Classification Search ............. 324/240, 324/233
See application file for complete search history.

(56) References Cited

U.S. PATENT DOCUMENTS 4,843,318 A * 6/1989 Greenblatt et al. .......... 324/225

| 5,552,704 A  | * | 9/1996 | Mallory et al.   | 324/233 |
| 6,344,741 B1 | * | 2/2002 | Giguere et al.   | 324/240 |
| 6,911,826 B2 | * | 6/2005 | Plotnikov et al. | 324/529 |

OTHER PUBLICATIONS

Sylvain Giguere et al, "Pulsed Eddy Current: Finding Corrosion Independently of Transducer Lift-Off", CP509 *Review of Progress in Quantitative Nondestructive Evaluation*, ©2000 American Institute of Physics, pp. 449-456.

J. S. R. Giguere et al, "Detection of Cracks Beneath Rivet Heads Via Pulsed Eddy Current Technique", CP615 *Review of Progress in Quantitative Nondestructive Evaluation* vol. 21, ©2002 American Institute of Physics, pp. 1968-1975.

B. A. Lepine et al, "Interpretation of Pulsed Eddy Current Signals for Locating and Quantifying Metal Loss in Thin Skin Lap Splices", CP615 *Review of Progress in Quantitative Nondestructive Evaluation* vol. 21, ©2002 American Institute of Physics, 0-7354-0061-X, pp. 415-422.

(Continued)

*Primary Examiner*—Reena Aurora
(74) *Attorney, Agent, or Firm*—Raggio & Dinnin, P.C.

(57) ABSTRACT

A method of eddy current testing without the need for lift-off compensation. Signal response features similar to those used in pulsed eddy current techniques are applied to conventional (harmonic) eddy current methods. The described method provides advantages in terms of data storage, since only two response parameters, the amplitude and phase, are sufficient to reconstruct any sinusoidal signal, therefore allowing for scanning of large surfaces.

10 Claims, 6 Drawing Sheets

OTHER PUBLICATIONS

S. Giguere et al, "Pulsed Eddy Current (Pec) Characterization of Material Loss in Multi-layer Structures", *Canadian Aeronautics and Space Journal*, vol. 46, No. 4, Dec. 2000, pp. 204-208.

S. Giguere et al, "Pulsed Eddy Current Technology: Characterizing Material Loss With Gap and Lift-Off Variations" *Res Nondestr Eval* (2001) 13, pp. 119-129.

J. H. V. Lefebvre et al, "Lift-Off Point of Intercept (LOI) Behavior", CP760 *Review of Progress in Quantitative Nondestructive Evaluation* vol. 24, ©2005 American Institute of Physics, pp. 523-530.

C. V. Donn et al, "Analytical Solutions to Eddy-Current Probe-Coil Problems", *Journal of Applied Physics*, vol. 19, No. 6, May 1968, pp. 2829-2838.

Catalin Mandache et al, "New Method for Lift-Off Independent Eddy Current Testing", Presentation, *NDE in the Land of Enchantment, ASNT 14$^{th}$ Annual Research Symposium*, Mar. 14-18, 2005, Hyatt Tamaya Resort, Albuquerque, NM, USA.

Catalin Mandache et al, "Time Domain Lift-Off Compensation Method for Eddy-Current Testing", *NDT.net*, Jun. 2005, vol. 10, No. 6, pp. 1-7.

C. Mandache et al, "Transient and Harmonic Eddy Currents: Lift-Off Point of Intersection", *NDT&E International 39* (2006), pp. 57-60.

B. P. Lathi, "Linear Systems and Signals". Oxford University Press, ©2002, pp. 435, 461, 462.

\* cited by examiner

METHOD AND APPARATUS FOR EDDY CURRENT DETECTION OF MATERIAL DISCONTINUITIES

This invention relates to a method and apparatus of eddy current testing and, in particular, to a method which compensates for variations in results due to probe lift-off.

BACKGROUND OF THE INVENTION

Non-destructive methods for determining material properties of solids are known in the art, and are commercially important, for example, for testing structural parts of aircraft, and other vessels, test and verification of production parts, structural pieces, et cetera. Eddy current testing is one well-known such method for determining material properties of solids that vary with magnetic and electrical properties of the material. In standard eddy current testing, a circular coil carrying an AC current is placed in close proximity to an electrically conductive specimen. The alternating current in the coil generates a changing magnetic field, which interacts with the test object and induces eddy currents therein. Variations in the phase and magnitude of these eddy currents can be monitored using a second "search" coil, or by measuring changes to the current flowing in the primary "excitation" coil. Variations in the electrical conductivity or magnetic permeability of the test object, or the presence of any flaws therein, will cause a change of eddy current flow and a corresponding change in the phase and amplitude of the measured current. This is the basis of standard eddy current inspection techniques.

It is also known to use pulsed excitation of the test coil for the detection and quantification of corrosion and cracking in multi-layer aluminum aircraft structures. Pulsed eddy current signals consist of a spectrum of frequencies, meaning that, because of the skin effect, each pulse signal contains information from a range of depths within a given test specimen. In addition, the pulse signal low-frequency components provide excellent depth penetration.

The response to a given input electric field depends on many factors, including the distance between the sample and the source of the electric field, and the distance between the sample and the detector of the response. The cumulative effect of the distances between the sample and the source and detector is referred to as lift-off U.S. Pat. No. 6,344,741 to Giguere et al. describes a method of eddy current testing in which a transmitter coil induces a magnetic field in a test object, when excited with a square wave current (pulse). The use of a square wave function produces a time-varying magnetic field and provides for a wide range of frequency excitation. The induced eddy currents flow at specific depths within the test object and decay over a period of time after the magnetic field being generated by the coil is terminated. Various sensors can be used to capture the time-domain variation of the magnetic flux.

U.S. Pat. No. 6,344,741 uses the fact that there is a point in time at which two or three lift-off balanced responses (defined with respect to a ½ cycle of the square wave) intersect. The patent teaches selecting a representative area of the structure that has no defect, to provide (at least two, but preferably three) calibration curves of balanced response signals at different lift-off points. The lift-off point of intersection is where the curves intersect. The time of occurrence of that lift-off point of intersection will be the same for any lift-off.

Applicants have found that, unexpectedly, similar constant lift-off point calculations can be used in sinusoidal eddy current testing. In this application Lift-Off point of Intersection (LOI) is used to refer to a phenomenon of a common point of intersection of response curves independently of the lift-off spacing. The LOI time can be detected by overlaying response curves of corresponding different lift-offs, with each response curve being aligned by a fixed relative off-set with respect to an input signal. Applicants investigated whether the LOI phenomenon recurred when different input excitation functions are used, and found that sinusoidally driven eddy currents also exhibit the common LOI. Applicants have provided an explanation for the basis of the existence of the LOI in the sinusoidally driven eddy currents based on a Fourier series decomposition of the square wave form. This explanation has been demonstrated in principle by aggregating response curves of a plurality of odd harmonic sinusoidal frequencies of a base frequency of a square wave function, and comparing the aggregate response with the response to the square wave function. In all cases a LOI is detected. The LOI is detected for a wide range of lift-off values, in the range of micrometers to millimeters.

SUMMARY OF THE INVENTION

Broadly speaking, the present invention relates to an eddy current detection method for locating flaws in an electrically conductive sample, comprising the steps of: a) providing sinusoidal excitation of the sample at a single RF frequency and measuring the response only at the single RF frequency as a function of time at one location; b) repeating the measuring step at least one more time at the same location for a different lift-off value; c) combining the responses to the measuring steps to determine a lift-off point of intersection (LOI) time point and a LOI response magnitude; d) performing at least one measurement of a magnetic response at another location on the sample to determine magnitude and phase of the response at the single RF frequency; and e) determining magnetic response magnitude at the LOI time point at the another location; whereby variation in the response magnitude at the LOI time point is used to indicate defects.

In another aspect, the invention relates to an eddy current detection method for locating flaws in an electrically conductive sample, comprising the steps of: a) providing sinusoidal excitation of the sample at a single RF frequency and measuring the response only at the single RF frequency as a function of time at one location; b) using the measurement with mathematical relationships to determine a lift-off point of intersection (LOI) time point and a LOI response magnitude for the sample; c) performing at least one measurement of a magnetic response at the single RF frequency; and d) determining magnetic response magnitude at the LOI time point at the another location; whereby variation in the response magnitude at the LOI time point is used to indicate defects.

DESCRIPTION OF THE PREFERRED EMBODIMENTS

Figure 1A:
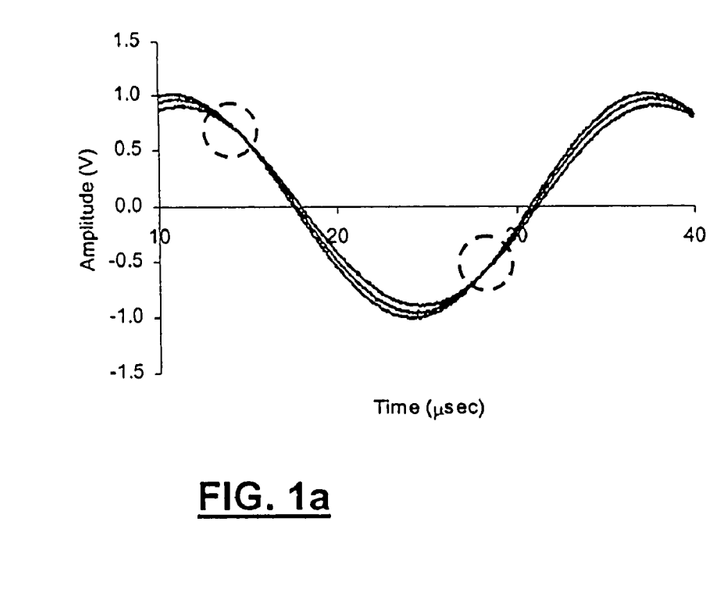
FIGS. 1a and 1b are response curves for sinusoidal excitation of the probe shown in FIG. 2.
Figure 1B:
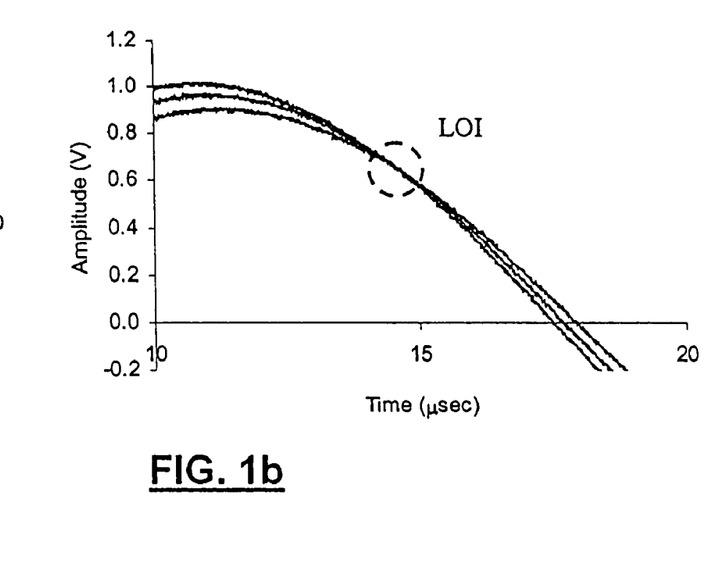

FIGS. 1a, and 1b show three response curves for sinusoidally driven eddy currents for three lift-off values. It is noted that each response curve traces out a sinusoid. Each response curve is temporally (phase or x-axis) aligned with the sinusoidal driving function, which is the same in each of the three cases. The y-axis represents the detected voltage, which represents the rate of change of the magnetic flux in the material. It will be appreciated that alternatively the magnetic field may be measured and a time derivative taken to obtain a similar result. The different sinusoids have slightly different amplitudes and phase off-sets, such that at they all intersect at two different phase times in each period. These two phase times are the LOI points. While only the response curves corresponding to lift-off values of 0, 0.254 mm, and 0.762 mm from the design lift-off of the probe are plotted, response curves corresponding to intermediate lift-off values also pass through these LOI points. The design lift-off is the distance between a tip of the probe and the bottom of the coil of the probe, as will be appreciated by those of skill in the art. The behavior of the curves in the neighborhood of the LOI points is shown in FIG. 1b.

Figure 2:
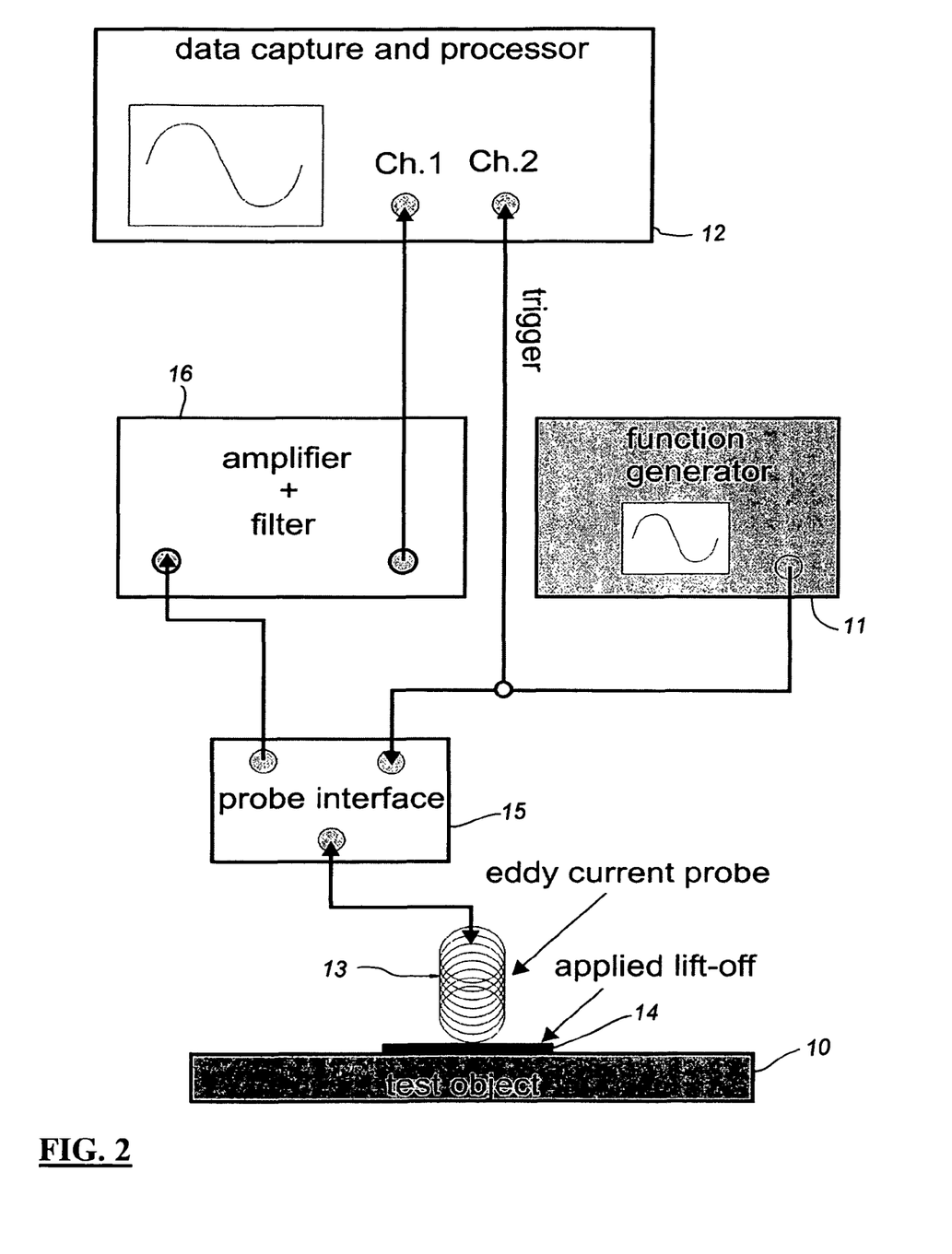
FIG. 2 is a schematic diagram of apparatus for carrying out the method of this invention.

The response curves shown in FIGS. 1a, and 1b are produced with the set-up schematically illustrated in FIG. 2. The conductive material or sample 10 is an aluminum block 280 mm long, 102 mm wide, and 12.7 mm thick. At the frequencies used with the configuration of the test apparatus, this conductive sample is effectively a semi-infinite plane. The sample conductivity was determined to be 45.88 percent International Annealed Copper Standard (% IACS). The apparatus includes a waveform generator 11 (Leader LFG-1300s) feeding a sinusoidal input signal to a probe. The input signal and the probe's response are recorded using a data capture and processor 12 (Tektronix TDS 5104 oscilloscope). The eddy current probe 13 has a single 300-turn absolute coil of nominal dimensions 3.1 mm thick and 9.5 mm outer diameter. The data processor 12 plots the response curve as a function of the sinusoidal driving function. This data is captured. To produce the three response curves shown in FIGS. 1a and 1b, response curves are captured with different spacers 14 between the probe and the sample.

Figure 3:
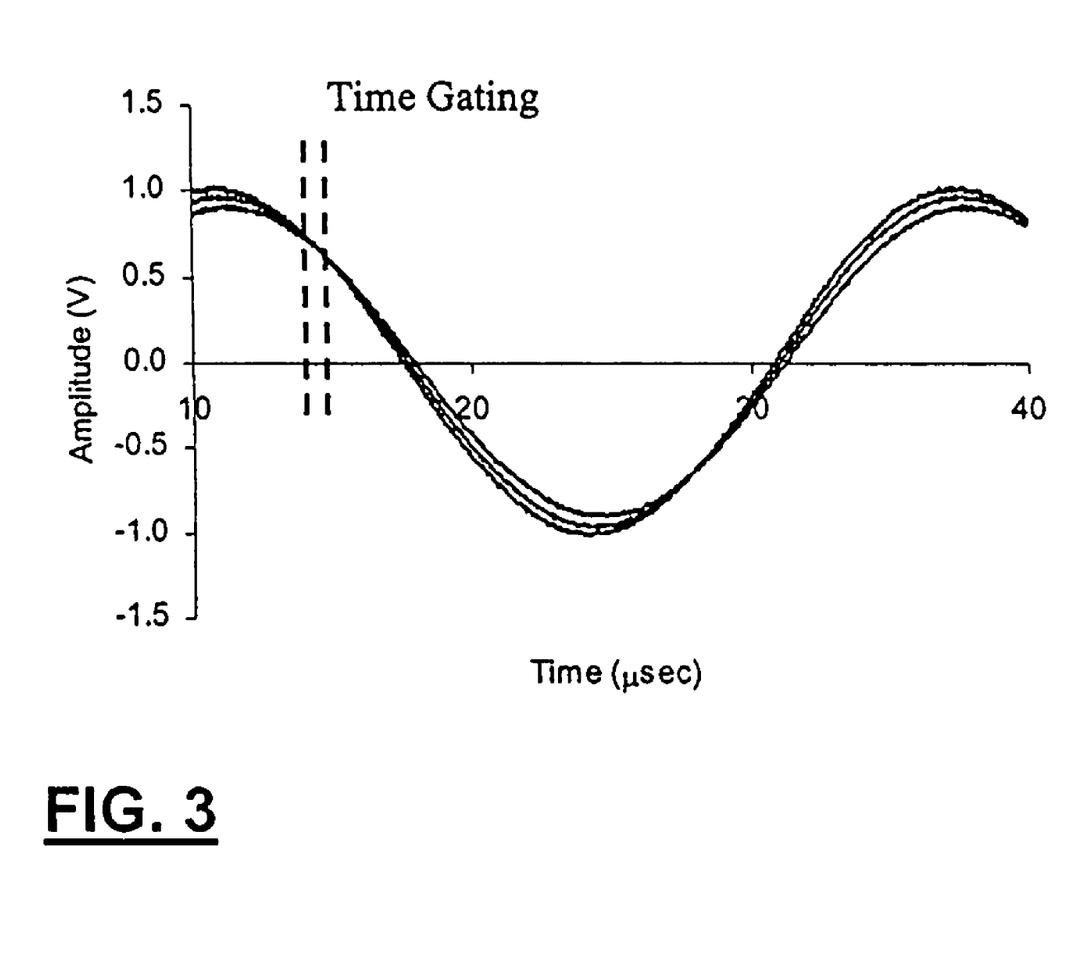
FIG. 3 is a further response curve illustrating the setting of a time gate.

It will be appreciated that once the LOI time and amplitude are determined, the apparatus may be used (without the spacer) to perform discontinuity testing. Such testing involves capturing response curves at corresponding locations of interest on the material, and determining the amplitude of the response curve at that time. This measured amplitude is compared with the LOI amplitude, as a difference between these amplitudes is an indicator of a discontinuity in the sample. One way to determine amplitude of the response curve at the LOI time is to time gate on the LOI time to inspect only the relevant values of the response curve. The response curve may be digitally smoothed, or may be synthesized in a particularly easy way because the response curve is a sinusoid. FIG. 3 schematically illustrates a time gate set at the LOI time and useful for detecting discontinuities for response curves at other locations that are likewise aligned to the sinusoidal input signal, and applied at the same amplitude.

The elements of FIG. 2 and their functional substitutes form an apparatus for eddy current testing. Probe 13 is coupled to a probe interface 15 through which the sinusoidal input signal is applied to the probe. Probe 13 serves to induce the magnetic field within the material, and to detect the response of the material. It will be appreciated that other mechanisms for inducing eddy currents within a sample can be used instead of a coil, and that multiple coils may be used. For example, probes consisting of a single input coil and a concentric response detector coil are known. In place of a coil, a Hall Effect device or other device may be used as a detector. The response is fed to data capture and processing device 12, which may consist of an oscilloscope and a computer. In FIG. 2 a commercially available amplifier and filter 16 is placed between the probe interface 15 and the data capture and processor 12 for amplifying the signal and filtering out noise from the response data in a manner well known in the art.

The response curve shown in FIGS. 1 and 3 varies with the response of the material to the sinusoidally driven induced eddy current. While the response curve amplitude may be current modulated, or any other type of modulated signal, typical probes emit a voltage modulated signal, which is amplified and filtered by the amplifier and filter 16. Accordingly the curve plotted in FIGS. 1a and 1b is a measured voltage, but its amplitude is arbitrarily chosen. It will be noted that the amplitude and temporal off-set induced by the experimental setup must remain constant between the computation of the LOI time and amplitude, and subsequent testing in order to obtain accurate evaluation of the response data.

The processor may further be adapted to derive the LOI time. The determination of the LOI time may be performed empirically or alternatively by solving an equation associated with the probe and the material. According to the empirical determination, an intersection of response curves aligned with the input signal is used, where each response curve corresponds to a different lift-off distance. This intersection may be obtained with the response data captured directly, by a smoothed or digitally filtered representation of the response data. The response data captured directly may be filtered to a sine function by a regression technique in order to obtain a phase off-set and an amplitude, which together are sufficient to completely characterize the response curve, as the response curve is a sinusoid of known frequency.

This method further involves computing multiple intersections to derive an LOI time with an established uncertainty. A record of uncertainty of the amplitude or phase off-set of the curve, and/or a measure of the fit of the curve to the sine function may also be stored. The aligning of the response curve with respect to a common reference trigger may involve triggering detection at a phase of an input signal that drives the induced eddy currents. The computing of an intersection of the response curves may further compute an uncertainty of the LOI time and/or a LOI amplitude.

The method for determining the LOI time and intensity may be performed using calibration measurements, or may be derived from a formula. The calibration measurements are performed on a part of the material that is expected to be free of discontinuities, or may be performed on a control or standard for the material that is known to be free of discontinuities. The method involves capturing responses of the material at multiple lift-off positions with respect to the same part of the material, and determining the LOI time and a voltage analog of the field intensity by identifying phase times with respect to the sinusoid at which each of the response curves achieves the same voltage. This can be performed by regression on the data point, by visual inspection of the response curves overlaid on top of each other, or by synthesizing an equation of the sinusoidal response curve to fit the data, and computing directly the intersection of the curves using equation (2) below.

Once the LOI time is established, response curves that are received are used to synthesize a sine function parameterized by an amplitude of the response curve, and a phase off-set. By doing so each response curve is adequately characterized by two values, rather than at least a few thousand data points defining each response curve. This permits a dramatic reduction of memory consumption, while permitting the data to be stored for reference purposes, or to make record of the test. It is possible to perform the reading step of the method only after a whole surface scan of the plate is complete. At this point each of the synthesized curves can be loaded in sequence while triggering the LOI time, resulting in one value for each point on the surface. This value can be color mapped and displayed directly, permitting quick and easy manipulation of the data.

Figure 4:
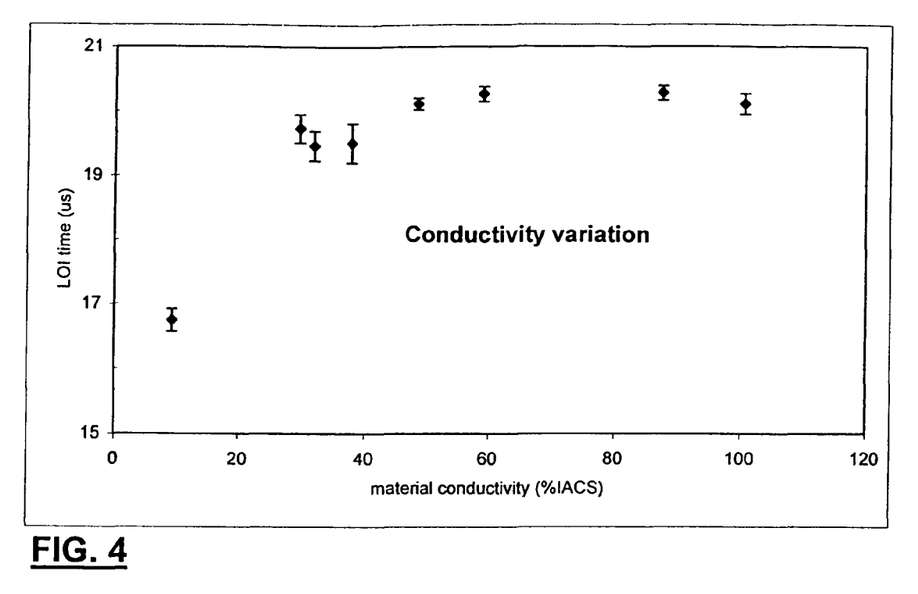
FIG. 4 and FIG. 5 are diagrams plotting the LOI time against sample conductivity and sample thickness.

Specific experiments have been conducted that demonstrate the existence of LOI time and amplitude as a function of conductivity and thickness of the material. FIG. 4 shows variation in LOI time of a plurality of samples having different conductivities, ranging from less than 10 percent to 100.58% IACS. The thickness of the samples was sufficient to effectively emulate a semi-infinite plane, given the input signal was a 24 kHz sinusoid. The experiment involved measuring the LOI time by varying the lift-off between a probe (a transducer that provided for both input of the magnetic field, and detector of magnetic flux) and the conductive sample. The LOI time was measured by comparing response curves at four lift-off values with respect to a design lift-off of the probe (specifically at 0, 0.254, 0.381, and 0.508 mm, respectively). The standard deviation of the LOI times, shown in the figures as a vertical bar, is recorded as the uncertainty of the LOI time, with a confidence of 95%. The voltage, which varies analogously with the response magnetic field of the sample, is also recorded. The LOI point is manifest when using material of a wide range of conductances.

Figure 5:
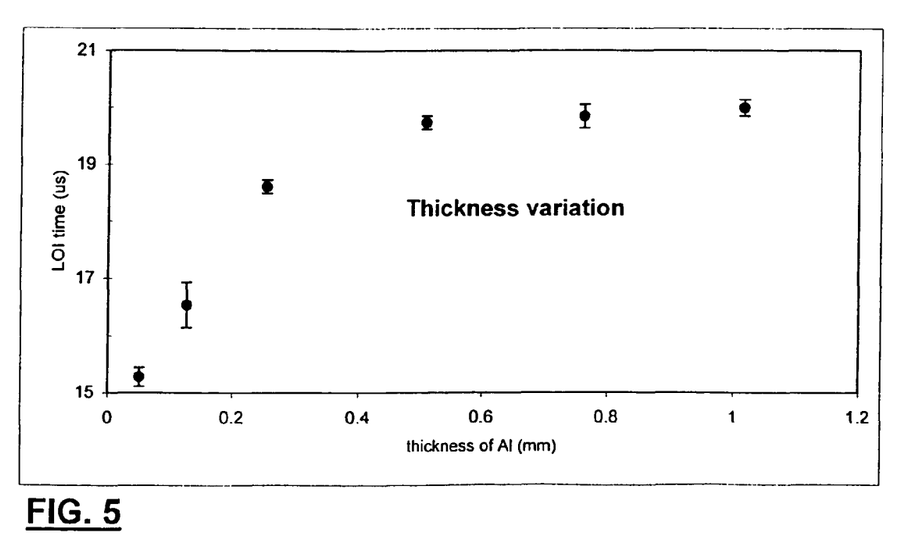

FIG. 5 shows results of testing of different thicknesses of aluminum (60% IACS) under similar test conditions as those of FIG. 1. The results clearly indicate that over a wide range of thicknesses the LOI point can be clearly identified. Thus, LOI points are observed when using sinusoidally driven eddy currents.

Figure 6A:
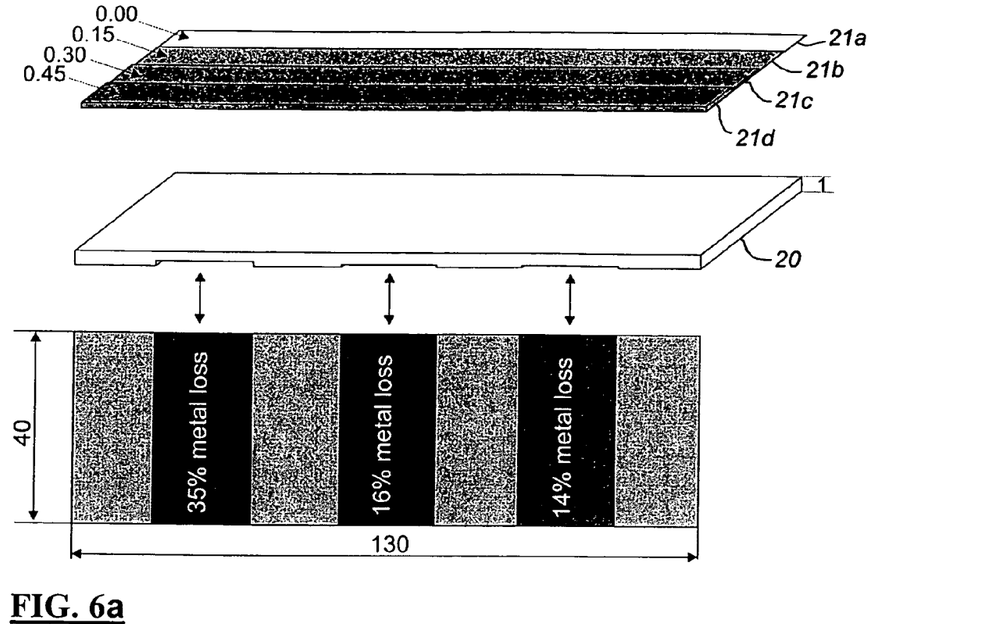
FIGS. 6a and 6b show test results for a sample of varying thickness.
Figure 6B:
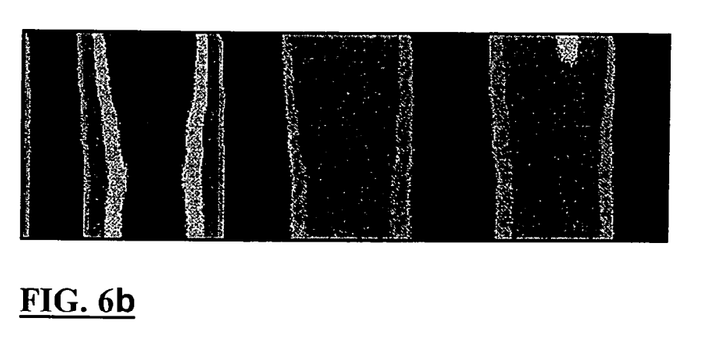

In FIG. 6a, a test layout is shown in which a slab of material 20 had three regions of material loss: one of 35%, one of 16% and one of 14%. On four strips 21a through 21d, each strip overlapping each of the regions, a respective spacer is provided. One of the strips provides a basic lift-off of the probe, and the other strips add separations of 0.15, 0.30, 0.45 mm, respectively. Scanning of the top surfaces with sinusoidally driven eddy currents over the strips produces a C-scan shown in FIG. 6b. The invariance of lift-off according to the technique is noted, as are the clarity of the results.

Figure 7A:
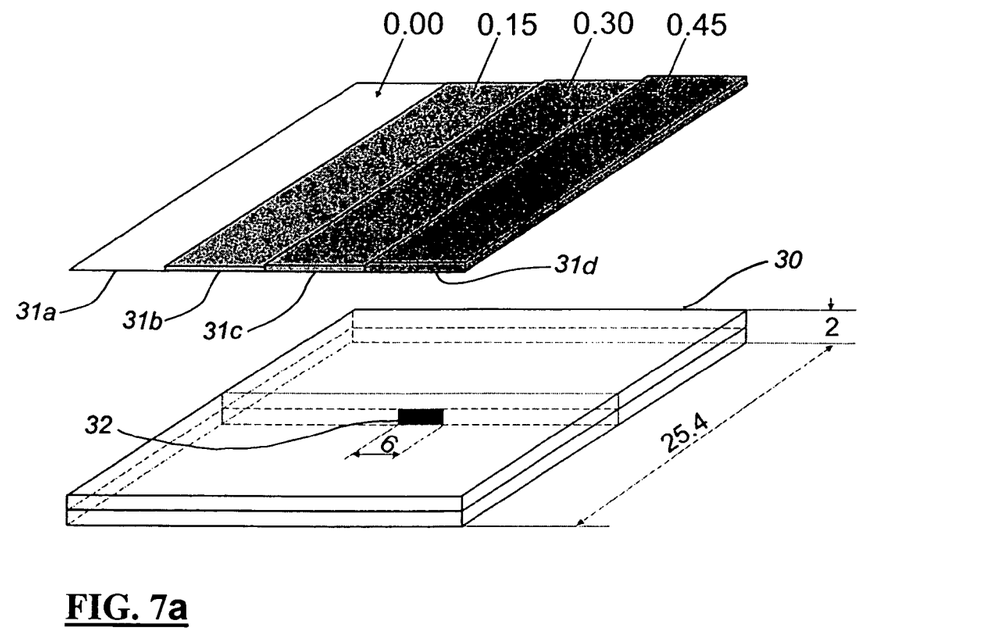
FIGS. 7a and 7b show test results for a sample containing a crack.
Figure 7B:
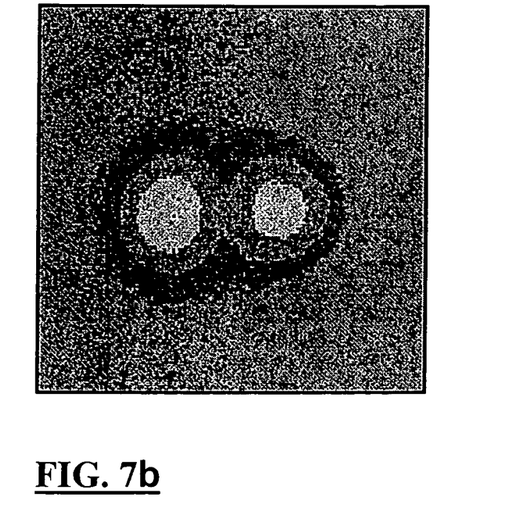

A detected crack 32 is tested at different lift-off values by placing different spacers 31a-31d between the coil and a top surface of the sample 30, as schematically illustrated in FIG. 7a. A C-scan of the sample is shown in FIG. 7b. It is noted that there are no bands evident on the C-scan indicating that the time points at which the measurements are made, are independent of the lift-off, and the variation of the response in the neighborhood of the LOI point near the crack is demonstrated.

The LOI points can also be obtained by calculation instead of by measurement. Returning to FIGS. 1a and 1b, the intersection time for any two sinusoidal outputs, $t_{LOI}$, can be obtained by solving equation (1) where $A_1$, $A_2$ and $\phi_1, \phi_2$ represent the amplitudes and the phases of any two response curves corresponding to different lift-off values, and $\omega$ is the frequency of the sinusoidal input signal.

$$A_1 \cdot \sin(\omega t_{LOI} - \phi_1) = A_2 \cdot \sin(\omega t_{LOI} - \phi_2) \quad (1)$$

$$t_{LOI} = \frac{1}{\omega} \cdot \tan^{-1}\left[\frac{A_1 \cdot \sin\phi_1 - A_2 \cdot \sin\phi_2}{A_1 \cdot \cos\phi_1 - A_2 \cdot \cos\phi_2}\right] \quad (2)$$

The time of intersection of any two sinusoidal signals of a same frequency and different phase and amplitude is provided using equation (2). Using equation (2), and the experimentally measured amplitude and phase for each lift-off and frequency, it is possible to generate a set of predicted synthetic LOI points. The results are shown in Table 1. It can be seen that there is agreement between the experimental and synthetic LOI point data. The relative error of the data points is less than 1.5%.

TABLE 1

| | Experimental LOI | | Synthetic LOI | |
|---|---|---|---|---|
| Frequency (Hz) | Time (μs) | Time between LOIs (μs) | Time (μs) | Time between LOIs (μs) |
| 12490 | 29.5 | 40.0 | 29.5 | 40.0 |
| 37560 | 14.6 | 13.3 | 14.4 | 13.3 |
| 62550 | 9.7 | 7.8 | 9.8 | 8.0 |
| 87550 | 7.3 | 5.7 | 7.1 | 5.7 |
| 112500 | 6.0 | 4.4 | 6.0 | 4.4 |

The LOI time determination may be generated from response curves performed on a part of the conductive material that is expected to be free of discontinuities, or may be formed on a control or a standard for the material that is known to be free of discontinuities. The determination may involve capturing responses of the material at three or more lift-off positions with respect to the same part of the material, so that verification of the LOI time can be made to a preferred accuracy. The determination of the LOI time can be performed by digital analysis of the response curves, by visual inspection of the response curves overlaid on top of each other, or by synthesizing an equation of the sinusoidal response curve to fit the data, and computing directly the intersection of the curves using equation (2), as previously noted.

REFERENCES

1. J. R. S. Giguère, J. M. S. Dubois, *Pulsed eddy current: finding corrosion independently of transducer lift-off*, Review of Progress in QNDE, Vol 19, pp. 449-456, 1999.
2. J. R. S. Giguère, B. A. Lépine, J. M. S. Dubois, *Detection of cracks beneath rivets via pulsed eddy current technique*, Review of Progress in QNDE, Vol. 21, pp. 1968-1975, 2001.
3. B. A. Lépine, J. R. S. Giguère, D. S. Forsyth, A. Chahbaz, J. M. S. Dubois, *Interpretation of pulsed eddy current signals for locating and quantifying metal loss in thin skin lap splices*, Review of progress in QNDE, Vol. 21, pp. 415-422, 2001.
4. S. Giguere, B. A. Lepine, J. M. S. Dubois, *Pulsed eddy current (PEC) characterization of material loss in multi-layered structures*, Canadian Aeronautics and Space Journal, Vol. 46 (4), pp. 206-208, 2000.
5. S. Giguere, B. A. Lepine, J. M. S. Dubois, *Pulsed eddy current technology: characterizing material loss with gap and lift-off variations*, Research in Nondestructive Evaluation, Vol. 13, pp. 119-129, 2001.

6. J. H. V. Lefebvre, J. M. S. Dubois, *Lift-off point of intercept (LOI) behaviour*, Review of Progress in QNDE, Vol. 24, 2005, pp. 523-530.
7. B. P. Lathi, *Linear Systems and Signals*, New York, Oxford University Press, 2.002;
8. C. V. Dodd, W. E. Deeds, *Analytical solutions to eddy-current probe-coil problems*, Journal of Applied Physics, Vol. 39, No. 6, pp. 2829-2838, 1968.
9. C. Mandache, J. H. V. Lefebvre, *New method for lift-off independent eddy current testing*, ASNT 14th Annual research Symposium, Albuquerque, N. Mex., 14-18 March 2005.
10. C. Mandache, J. H. V. Lefebvre, M. Brothers, *Time Domain lift-off compensation method for eddy current testing*, e-journal of NDE, www.ndt.net, 2005, vol 10 no 6.
11. C. Mandache, J. H. V. Lefebvre, *Transient and Harmonic Eddy Currents: Lift-off Point of Intersection*, NDT&E International, 2006, Vol 39, p 57-60.

What is claimed is:

1. An eddy current detection method for detecting discontinuities in an electrically conductive sample, comprising the steps of:
    a) providing sinusoidal excitation of the sample at a single frequency and measuring the response only at a single frequency as a function of time at one location,
    b) repeating the measuring step at least one more time at the same location for a different lift-off value,
    c) combining the responses to the measuring steps to determine a lift-off point of intersection (LOI) time point and a LOI response magnitude,
    d) performing at least one measurement of a magnetic response according to a) at another location on the sample without regard to lift-off to determine magnitude and phase of the response at a single frequency, and
    e) determining magnetic response magnitude at the LOI time point at the said another location,
    whereby variation in the response magnitude at the LOI time point is used to indicate defects.

2. The method as set out in claim 1 wherein steps d) and e) are repeated across the sample and the results stored in memory.

3. The method as set out in claim 1 further including the step of:
    f) inspecting only a particular time segment of the response of step d) corresponding to the expected location of the LOI time point.

4. The method as set out in claim 1 wherein step d) occurs without computing a lift-off at the other location during the measurement.

5. The method as set out in claim 1 further including the step of using the same probe to provide for independent eddy current detection.

6. An eddy current detection method for detecting discontinuities in an electrically conductive sample, comprising the steps of:
    a) providing sinusoidal excitation of the sample at a single frequency and measuring the response only at a single frequency as a function of time at one location,
    b) using the measurement with mathematical relationships to determine a lift-off point of intersection (LOI) time point and a LOI response magnitude for the sample,
    c) performing at least one measurement of a magnetic response at another location on the sample without regard to lift-off to determine magnitude and phase of the response at the single frequency, and
    d) determining magnetic response magnitude at a LOI time point at the said another location,
    whereby variation in the response magnitude at the LOI time point is used to indicate defects.

7. The method as set out in claim 6 wherein steps c and d) are repeated across the sample and the results stored in memory.

8. The method as set out in claim 6 further including the step of:
    e) inspecting only a particular time segment of the response of step c) corresponding to the expected location of the LOI time point.

9. The method as set out in claim 6 wherein step c) occurs without computing a lift-off at the other location during the measurement.

10. The method as set out in claim 6 further including the step of using the same probe to provide for independent eddy current detection.

* * * * *

UNITED STATES PATENT AND TRADEMARK OFFICE
CERTIFICATE OF CORRECTION

PATENT NO.         : 7,750,626 B2
APPLICATION NO.    : 11/372126
DATED              : July 6, 2010
INVENTOR(S)        : J. H. Vivier Lefebvre et al.

It is certified that error appears in the above-identified patent and that said Letters Patent is hereby corrected as shown below:

Column 5, Line 66, please replace "$\omega is$" with "$\omega\ is$" after lift off values, and Column 6, Line 33, please replace the word "formed" with "preformed" before on a control Signed and Sealed this Thirty-first Day of August, 2010

David J. Kappos
*Director of the United States Patent and Trademark Office*